(12) United States Patent  (10) Patent No.: US 8,827,088 B1
Krause et al.  (45) Date of Patent: Sep. 9, 2014

(54) WEDGE-LOCK BRACKET FIXATION

(75) Inventors: John D. Krause, Austin, TX (US); Don E. McGee, Fisher, IN (US)

(73) Assignee: Greatbatch Ltd., Clarence, NY (US)

( * ) Notice: Subject to any disclaimer, the term of this patent is extended or adjusted under 35 U.S.C. 154(b) by 172 days.

(21) Appl. No.: 13/300,696

(22) Filed: Nov. 21, 2011

Related U.S. Application Data

(60) Provisional application No. 61/415,445, filed on Nov. 19, 2010.

(51) Int. Cl.
*A61L 2/26* (2006.01)

(52) U.S. Cl.
USPC .......... 211/85.13; 248/310; 422/297; 422/300

(58) Field of Classification Search
CPC .................................. A61L 2/26; A61B 19/02
USPC ........................ 206/370, 572; 422/297, 300;
248/220.31, 309.1, 310, 311.2, 316.2,
248/316.7, 682; 211/85.13, 89.01, 124
See application file for complete search history.

(56) References Cited

U.S. PATENT DOCUMENTS

| | | | |
|---|---|---|---|
| 3,022,973 A * | 2/1962 | Morrow et al. .......... 248/220.22 |
| 4,762,688 A | 8/1988 | Berry, Jr. |
| 4,798,292 A * | 1/1989 | Hauze ............................ 206/439 |
| 5,012,997 A * | 5/1991 | Hutchison ................. 248/220.41 |
| 5,082,215 A * | 1/1992 | Hutchison ................. 248/220.22 |
| 5,174,453 A * | 12/1992 | Stoeffler ....................... 206/570 |
| 5,346,075 A * | 9/1994 | Nichols et al. .............. 211/60.1 |
| 5,384,103 A | 1/1995 | Miller |
| 5,599,512 A | 2/1997 | Latulippe et al. |
| 5,681,539 A * | 10/1997 | Riley ............................ 422/300 |
| 5,993,754 A * | 11/1999 | Lemmen et al. .............. 422/293 |
| 6,003,685 A * | 12/1999 | Malin ................................ 211/7 |
| 6,048,503 A * | 4/2000 | Riley et al. .................... 422/298 |
| 6,099,812 A | 8/2000 | Allen et al. |
| 6,193,932 B1 * | 2/2001 | Wu et al. ......................... 422/28 |
| 6,382,575 B1 | 5/2002 | Frush et al. |
| 6,585,942 B1 * | 7/2003 | Bussell et al. ................. 422/300 |
| 6,969,498 B1 * | 11/2005 | Riley ............................ 422/300 |
| 7,131,542 B2 * | 11/2006 | Sedon et al. ................. 211/59.1 |
| 7,147,114 B2 * | 12/2006 | Sarnoff et al. ............. 211/90.03 |
| 7,601,312 B2 * | 10/2009 | Riley et al. .................... 422/300 |
| 7,717,264 B2 * | 5/2010 | Bettenhausen et al. ....... 206/370 |
| 8,069,998 B2 * | 12/2011 | Thomas ..................... 211/85.13 |
| 8,272,508 B2 * | 9/2012 | Bettenhausen et al. ....... 206/370 |
| 8,307,995 B2 * | 11/2012 | Surma et al. ....................... 211/7 |
| 8,341,987 B2 * | 1/2013 | Nagelski ......................... 70/276 |
| 8,542,119 B2 * | 9/2013 | Sankey ....................... 340/568.1 |

(Continued)

FOREIGN PATENT DOCUMENTS

FR 2907661 5/2008

*Primary Examiner* — Terrell McKinnon
*Assistant Examiner* — Eret McNichols
(74) *Attorney, Agent, or Firm* — Steven W. Winn

(57) ABSTRACT

A support bracket for holding, securing and portioning orthopedic tools and/or devices within a case or tray is described. Multiple support brackets creating a modular system of brackets may be used within the case. Each support bracket is designed to releasably lock within an opening of a floor of the tray or case. The support bracket comprises a support member having opposing sidewall surfaces that upwardly extend from a base portion. A bracket insert, having a bottom wall extending distally from a sidewall, is positionable within a passageway formed within a bottom surface of the base portion to thereby lock the support bracket in position within the tray.

29 Claims, 13 Drawing Sheets

(56) References Cited

U.S. PATENT DOCUMENTS

| | | | |
|---|---|---|---|
| 2002/0071799 A1* | 6/2002 | Wood | 422/300 |
| 2002/0074253 A1* | 6/2002 | Allen et al. | 206/370 |
| 2004/0026344 A1* | 2/2004 | Sedon et al. | 211/7 |
| 2005/0161355 A1* | 7/2005 | Matthis et al. | 206/370 |
| 2006/0067661 A1* | 3/2006 | Pierzynski et al. | 396/71 |
| 2007/0205123 A1* | 9/2007 | Bettenhausen et al. | 206/363 |
| 2008/0149512 A1* | 6/2008 | Dane | 206/370 |
| 2008/0314789 A1 | 12/2008 | Thomas | |
| 2009/0173853 A1* | 7/2009 | Fawcett et al. | 248/220.31 |
| 2010/0176016 A1* | 7/2010 | Pell | 206/370 |
| 2014/0083886 A1* | 3/2014 | Winterrowd et al. | 206/370 |

* cited by examiner

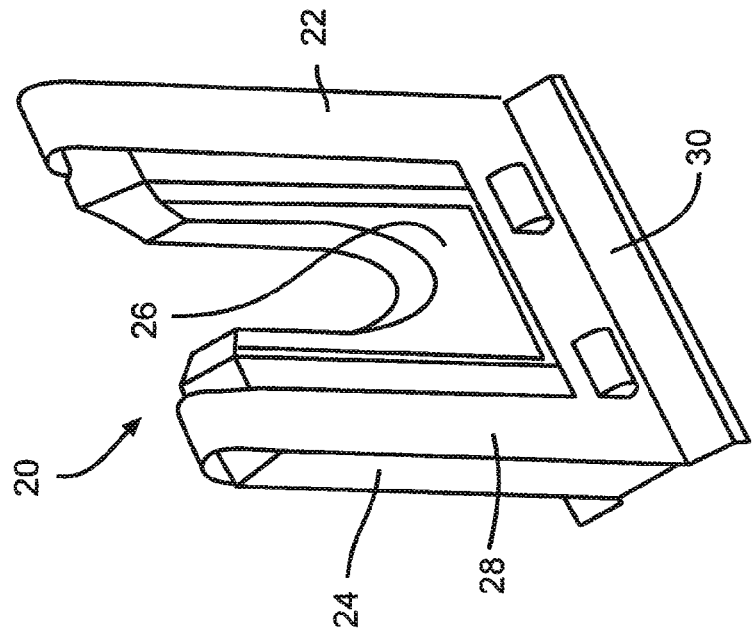
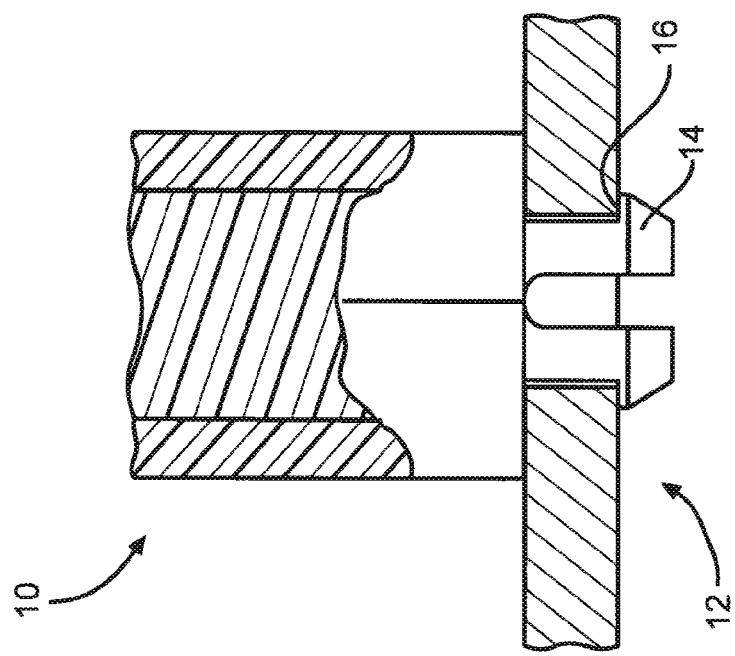

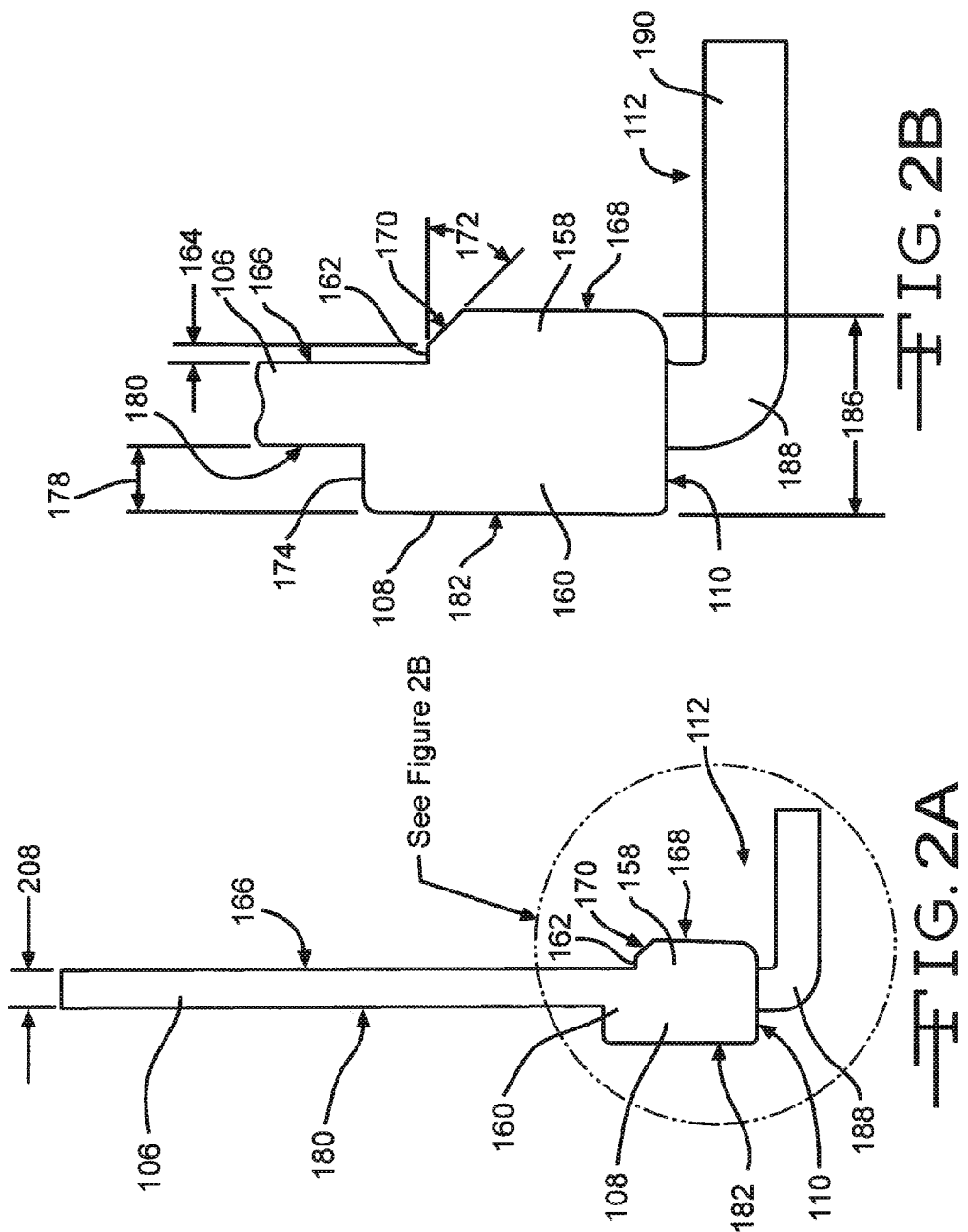

WEDGE-LOCK BRACKET FIXATION

CROSS REFERENCE TO RELATED APPLICATIONS

This application claims priority to U.S. provisional application Ser. Nos. 61/415,445, filed on Nov. 19, 2010.

BACKGROUND OF THE INVENTION

1. Field of the Invention

The present invention is related generally to orthopedic cases and trays. More specifically, the present invention is related to a bracket designed to partition and/or hold orthopedic tools and devices therewithin.

2. Background Art

In the sterilization of surgical instruments it is desirable to have a sterilization tray assembly, which will support the instruments during sterilization and can also be used for transporting and storing the instruments after sterilization. As instruments become larger and more complex, such as those used in endoscopy and orthoscopic procedures, it is necessary to provide a support having resilient contact with the surgical instrument and which can be securely positioned within the tray so that it will not be displaced during handling of the tray. Due to the appreciable weight and size of the surgical instruments, this support may be subjected to considerable stress.

Since surgical instruments come in a wide variety of shapes and sizes, and since it is impractical to have a single tray devoted to a particular type of surgical instrument, the art has developed numerous systems wherein supports for the surgical instruments can be provided in a modular form. A number of these various modules are designed such that they can be selectively positioned within a tray, for example, by plugging portions of the support elements through holes in a portion of the tray. The support elements can thus be arranged to match the shape of the surgical instrument to be sterilized.

One such bracket system is disclosed in U.S. Pat. No. 5,599,512 to Latulippe et al. As shown in FIG. 1A, Latulippe discloses a modular support bracket 10 with an anchor structure 12 comprising opposing fingers 14 and a narrow shoulder 16. This anchor structure 12 is designed to secure itself with the floor of a tray. This opposing finger 14 and narrow shoulder 16 feature of Latulippe provides a re-positionable bracket, however, it has inadequate strength and rigidity to support orthopedic tools, particularly those tools and devices which are of substantial weight and size. Given the increased weight and size of some orthopedic tools and devices, an anchor 12, such as that of Laulippe et al., could easily break off under the weight and added stress of these tools.

Furthermore, over time and use, the Laulippe et al, anchor structure 12 is particularly prone to mechanical fatigue and distortion. Such mechanical fatigue could lead to the structural degradation or even breakage of the anchor fingers 14 and/or shoulders 16. Structural distortion of the Laulippe et al. anchor 12 could prevent the bracket 10 from securely interfacing with the floor of the case. Thus, the Laulippe et al. bracket system may not adequately secure the tools and devices therewithin.

Another such bracket system is disclosed by Frush et al. in U.S. Pat. No. 6,382,575. Frush discloses a modular support bracket 20 with an anchor structure that secures the bracket 20 to the floor of a tray. As shown in FIG. 1B, the Frush anchor structure comprises a clip 22 that is fitted over two opposing posts 24 of a support structure 26 of the bracket 20. As the figure shows, the clip 22 is positioned over the bracket 20 such that the legs 28 of the clip 22 are supported by the opposing posts 24. Once positioned over the bracket posts 24, a flange 30 residing between each of the legs 28 secures the bracket to the floor of a tray. The repositionable Frush bracket 20 is limited in that it requires a bracket 20 with the opposing posts 24 with which the clip 22 secures thereto.

In addition, the Frush invention is limited in that the opposing flange 30 design requires that the bracket 20 be secured and released from beneath the floor of the tray through manipulation, i.e. squeezing together of the opposing flanges 30. Per Frush, the bracket 20 is inserted and removed from beneath the floor of the tray. Therefore, the use of the Frush bracket 20 is limited for use with a single layer tray. The anchor clip design of the Frush bracket 20 prohibits its use with double well or other multiple layered style trays or cases.

Unlike the Frush bracket, the bracket and bracket system of the present invention does not have these limitations. Since the anchor portion of the present invention is positioned between the bracket and the floor surface of a case or tray, its anchoring mechanism is independent of the bracket support member structure or case design. The design of the support member portion of the bracket of the present invention is unlimited and may comprise for example, an "L" shape, a "V" shape or a "U" shape with or without opposing posts.

Therefore, there is a need for a support bracket and encompassing system with improved mechanical durability that is easily repositionable in a multitude of orientations. In addition, there is a need for an improved bracket system that provides for support of larger, heavier tools and devices. And furthermore, there is a need for a support bracket that allows for unlimited design iterations and is unencumbered by support member limitations that confine the brackets ability to hold and support an orthopedic tool or device.

SUMMARY OF THE INVENTION

The present invention, therefore, provides for a support bracket designed to hold and partition a wide array of orthopedic tools and devices of various geometries and weights within a case or tray. The support bracket can be positioned in a number of non-limiting orientations such as in a horizontal, a vertical or a diagonal position within the case. Furthermore, the support bracket of the present invention is designed with a quick release anchor mechanism that enables each of the support brackets to be easily removed and, subsequently, securely repositioned within the case.

The support bracket of the present invention may be a modular system comprised of a plurality of support brackets configured in a variety of differing shapes and sizes designed to accommodate a wide variety of orthopedic tools and/or devices. Specifically, each support bracket of the present invention comprises a support member and a bracket anchor portion. The support member and the bracket anchor portion are designed to work in concert to secure the support bracket or plurality of support brackets to a case floor.

The anchor portion secures the support member to the topside of the floor of a case or tray. The anchor portion preferably comprises a set of legs that extend from the bottom of its anchor portion. The legs are preferably oriented parallel to each other and in a perpendicular orientation to the support member. The legs of the anchor portion are designed to fit through a slot opening of the floor of a case such that the legs reside underneath the floor surface, thereby preventing the support bracket portion from becoming dislodged or removed from the case or tray floor.

A bracket insert is further positioned between the bottom of the support member and the floor surface, thereby securing the support bracket to the case. The bracket insert comprises an angled raised portion with a series of ridges that are designed to form a secure interference fit between the bracket and the floor surface thus preventing the bracket from moving and becoming unsecured from the case.

The support member of the bracket extends upwardly from the anchor portion. The support member further comprises an opposing wall structure of various geometries that is preferably positioned perpendicular to the floor of the case or tray. As will be discussed in more detail, the support member of the bracket may be shaped in a multitude of non-limiting shapes such as an "L", "V", or "U" shape. In addition, the support member portion may be designed such that it comprises a combination of a multitude of non-limiting shapes, such as an "L", "V", or "U" shape. Furthermore, the support bracket system of the present invention may be secured with a plurality of anchor portions.

BRIEF DESCRIPTION OF THE DRAWINGS

FIG. 1A illustrates an embodiment of a prior art orthopedic tool support bracket.

FIG. 1B shows an alternate embodiment of a prior art orthopedic tool support bracket.

FIGS. 2A and 2B show magnified cross sectional views of various features of the support bracket shown in FIG. 2.

DETAILED DESCRIPTION OF THE PREFERRED EMBODIMENTS

Turning now to the drawings, FIGS. 2 and 5 through 11, illustrate a support bracket 100 according to the present invention. The support bracket 100 is designed to be connectable to an orthopedic tool tray or case 102 (FIG. 12). The support bracket provides a means for various orthopedic tools and/or devices (not shown) to be securely held therewithin. In addition, the support bracket 100 of the present invention provides a means for partitioning various orthopedic tools and/or devices (not shown) from each other therewithin. In a preferred embodiment, a plurality of support brackets 100 may be secured within the case providing a modular system of support brackets 104 (FIG. 12).

Figure 2:
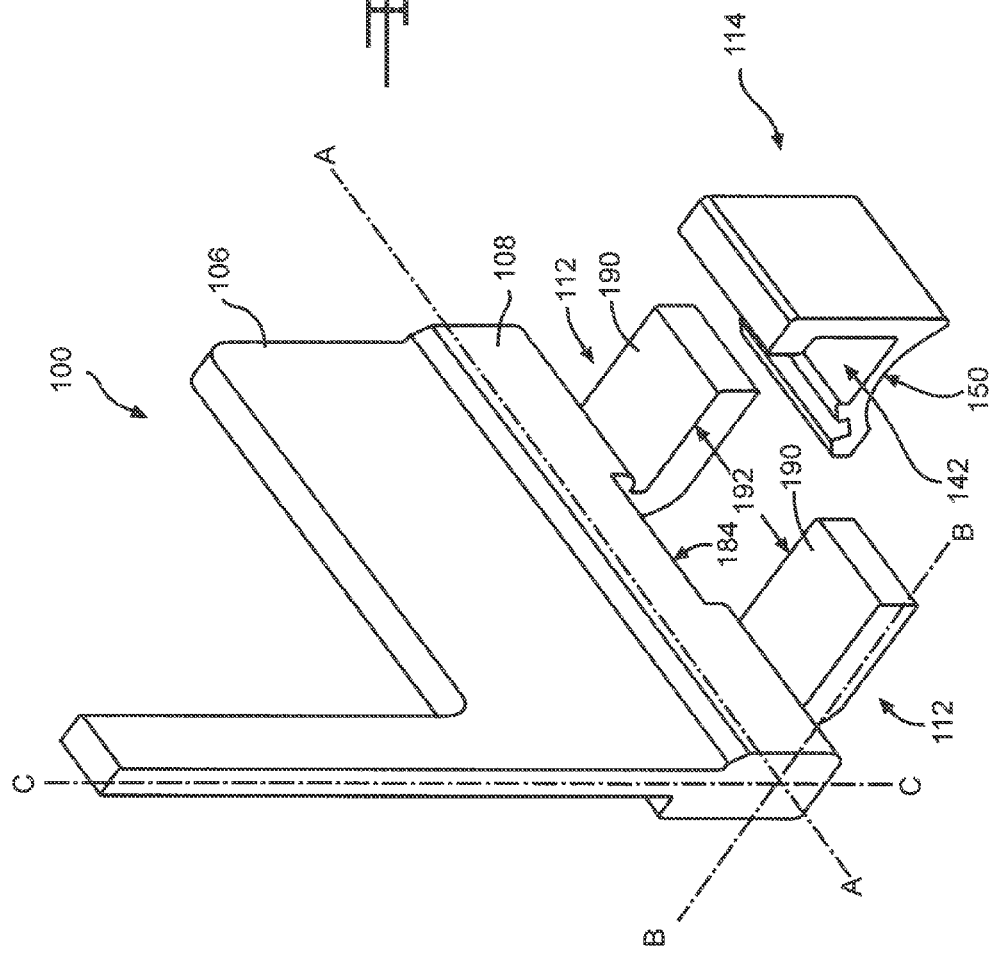
FIG. 2 illustrates a perspective view of an embodiment of a support bracket of the present invention.

FIG. 2 illustrates an exemplary embodiment of the support bracket 100 of the present invention. As shown, the support bracket 100 has a length that extends about parallel to a longitudinal axis A-A. In addition, the support bracket 100 has a width extending about parallel to axis B-B that is perpendicular to longitudinal axis A-A, and a height extending about parallel to axis C-C.

The support bracket 100 comprises a support ember 106 having opposing sidewall surfaces, the sidewall having a height that extends upwardly from a base portion 108 of the support bracket 100 along axis C-C. The support member 106 further has a length that extends laterally along longitudinal axis A-A and a width that extends along axis B-B.

Extending away from a bottom surface 110 of the base portion 108 is a leg or legs 112. The legs 112 comprise a feature of an anchor mechanism that helps secure the bracket 100 to the case 102. In addition to the support bracket legs 112, the anchor mechanism further comprises a bracket insert 114. The bracket insert 114 is designed to work in concert with the legs 112 to provide a secure connection between the support bracket 100 and the case 102. As shown in FIGS. 2, 2A and 2B, the anchor portion is designed to be connectable to a surface of the case or tray 102, thereby securing the support bracket 100 therewithin. More preferably, the anchor portion is connectable to a floor 116 of the case or tray 102 (FIG. 12).

In an embodiment, the support bracket 100 of the present invention, including its associated components comprising the support member 106 and bracket insert 114, are preferably composed of a polymeric material such as polyethylene, or polyether ether ketone (PEEK), or the like. Such a preferred material provides the support bracket 100 and its associated components with a flexible yet durable structure that is capable of supporting a variety of orthopedic tools and devices.

In a preferred embodiment, the bracket insert 114 is positionable between the support member and the floor of the case within the anchor portion to provide a secure connection therebetween. Furthermore, the support bracket 100 may be positioned in a multitude of non-limiting orientations within the tray or case 102, such as in a vertical, horizontal or diagonal orientation with respect to imaginary axis C-C along the case floor 116.

As shown in FIGS. 2, 3 to 11, the bracket insert of the present invention is generally of an "L" shape. The bracket insert 114 comprises an insert proximal end portion spaced from an insert, distal end portion. More specifically, the insert 114 comprises an insert bottom wall 118, having an insert proximal end portion 120 spaced apart from an insert distal end portion 122 that is oriented about perpendicular to an insert sidewall 124. In a preferred embodiment, the insert sidewall 124 is fluidly connected to the insert bottom wall 118 such that the proximal end 120 of the bottom wall 118 is connected to a bottom portion of the sidewall 124 of the insert 114.

The distal end portion 122 of the bottom wall 118 is preferably angled in a downward direction with respect to its proximal end portion 120. In a preferred embodiment, the distal end portion of the bottom wall 118 is angled at an insert, distal end angle 126 that ranges from about 20° to about 50°, more preferably about 30°. The insert distal end angle 126 is herein defined as the intersection of an insert longitudinal axis D-D and imaginary line E-E that extends tangentially along a top surface of the distal end of the insert 114 (FIG. 3).

Figure 3:
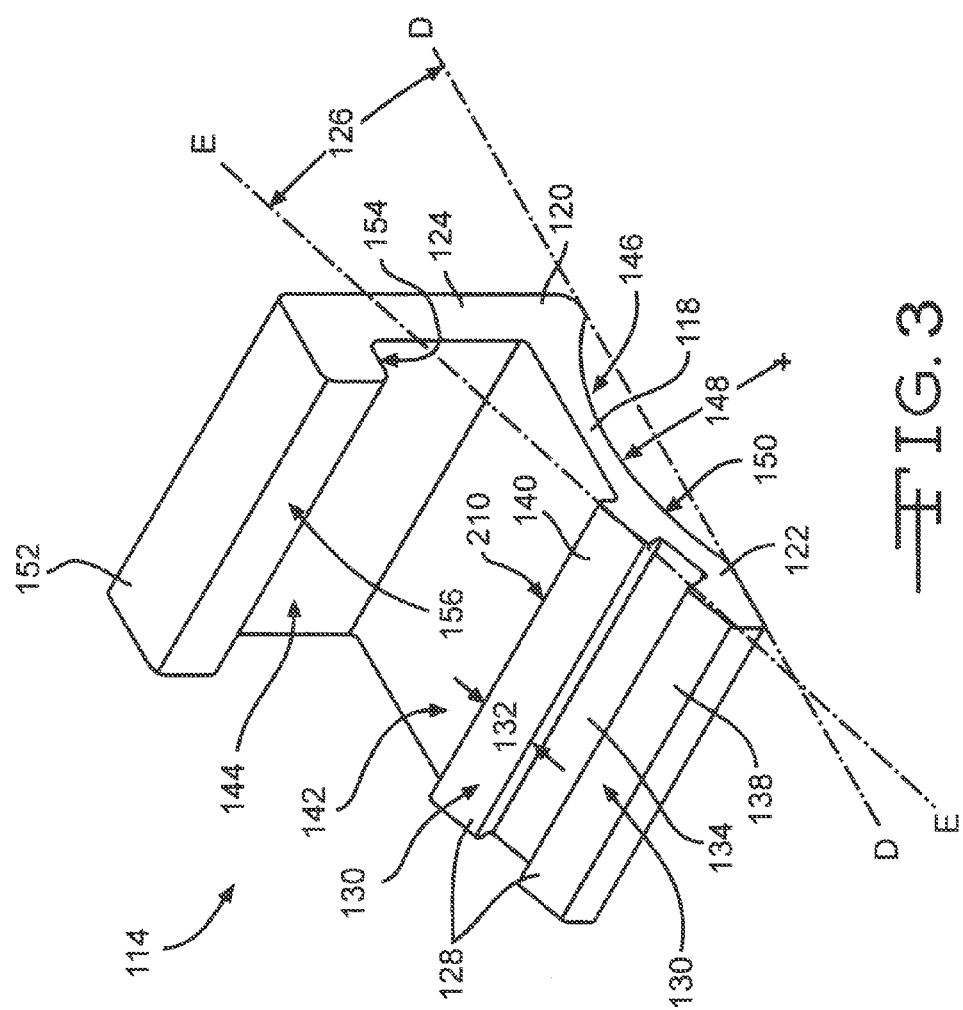
FIG. 3 illustrates a perspective view of an embodiment of a bracket insert that is used in conjunction with the support bracket of the present invention.

As shown in FIGS. 3 to 11, the distal end 122 of the insert 114 further comprises a series of ridges 128 that span the width of the angled distal end portion 122 of the bottom wall 118. These ridges 128 are designed such that they each have a ridge height ranging from about 0.02 cm to about 0.5 cm with a raised ridge surface 130 having a ridge width 132 preferably ranging from about 0.10 cm to about 0.50 cm. In a preferred embodiment, a trough 134 having a trough width 136 ranging from about 0.10 cm to about 0.50 cm resides between adjacent ridges 128. Each ridge 128 preferably spans the width of the distal end of the bottom wall 118. In a preferred embodiment, as shown in FIG. 3, there are two ridges, a first ridge 138 that resides distal of a second ridge 140.

Figure 4:
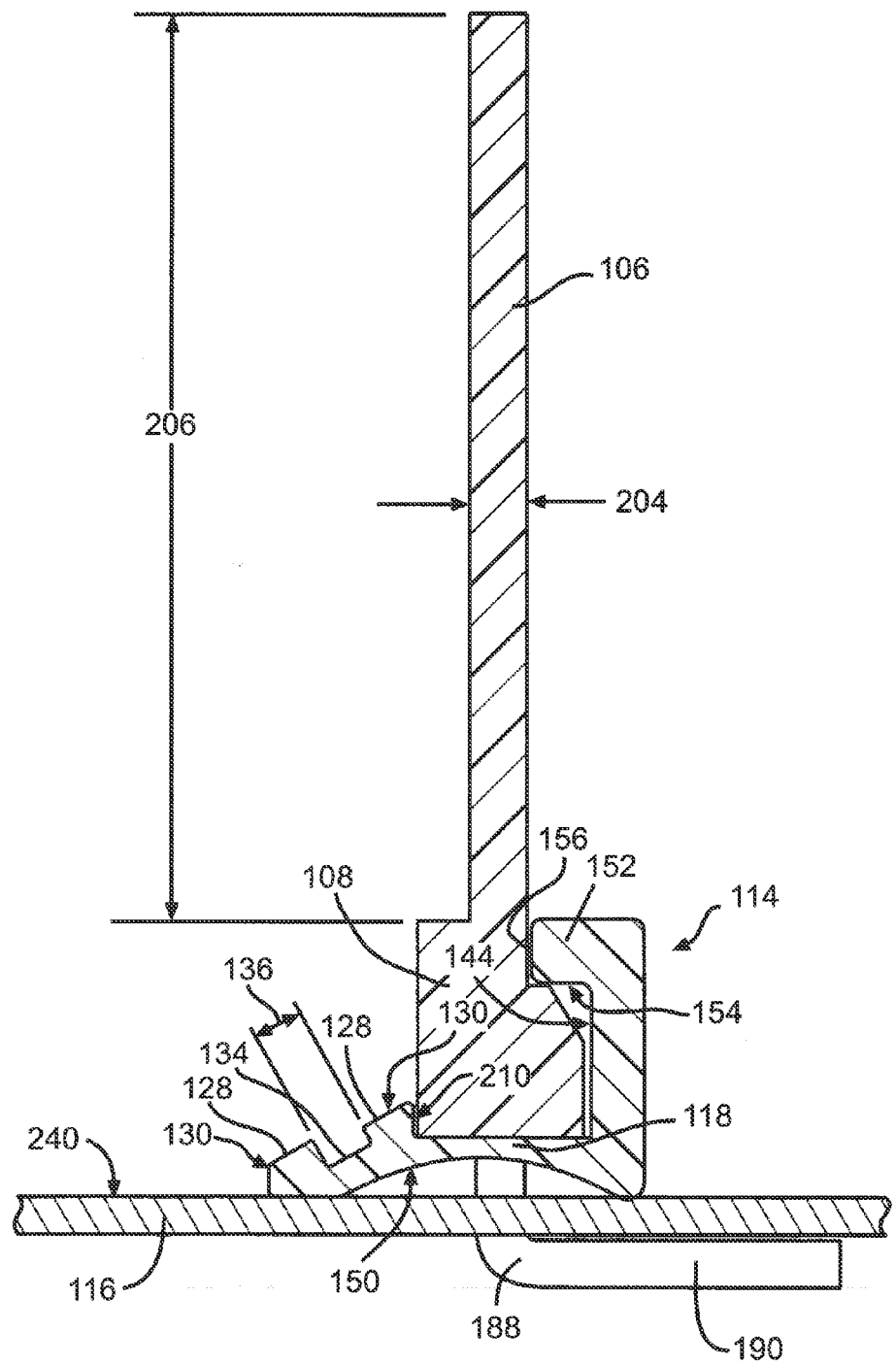
FIG. 4 is a cross-sectional view of the support bracket of FIG. 2 securely positioned within a tray or case.

As illustrated in FIGS. 3 and 4, the bracket insert 114 further comprises a landing surface 142 that resides along a portion of a top surface of the bottom wall 118. In a preferred embodiment, the landing surface 142 resides between the second insert ridge 140 and an inner sidewall surface 144 along the top surface of the bottom wall 118. It is preferred that the landing surface 142 has a planar surface that extends about parallel with longitudinal axis D-D (FIG. 3).

In a preferred embodiment, the insert 114 comprises an archway 146 with an arc insert radius of curvature 148 that, partially extends within a bottom surface 150 of the bottom wall 118 of the insert 114. The archway 146 is positioned such that its radius is partially bounded by the distal and proximal ends of the bottom wall of the insert 114. In a preferred embodiment, the arc insert radius of curvature 148 ranges from about 0.5 cm to about 3 cm. The archway 146 is design such that it provides mechanical flexibility to the insert 114. Specifically, the archway 146 provides an upward bias force to the landing surface 142. When positioned between the support member 106 and the floor 116 of a tray 102, the archway 146 provides a bias force in an upwardly direction that secures the bracket insert 114 and the contacting support member 106 to the case 102. In other words, the bias force provided by the archway 146, "wedges" the bracket insert therewithin thus preventing the support bracket 100 from moving.

As illustrated in FIGS. 3 to 11, the bracket insert. 100 further comprises an overhang or lip portion 152 that extends along the width of the insert 114. The overhang portion 152 is preferably positioned at the top portion of the insert sidewall 124. The overhang 152 is further positioned such that it protrudes outwardly from the inner surface 144 of the sidewall 124 of the insert 114. In a preferred embodiment, the overhang portion 152 protrudes about 0.1 cm to about 0.5 cm from the inner surface 144 of the sidewall 124. The overhang portion preferably has an overhang bottom surface 154 that is oriented about perpendicular to an overhang side surface 156.

Now turning to FIGS. 2, 2A, 2B and 4, these drawings illustrate the base portion 108 of the support member 106. As illustrated, the base portion 108 of the support member 106 serves as a footing for the support bracket 100. A bottom surface of the base portion 108 contacts the floor 116 of the case 102. In addition, the base portion 108 provides surfaces with which the bracket insert 114 interface and secures thereto. In a preferred embodiment, the base portion comprises a base portion front protrusion 158 spaced apart from a base portion rear protrusion 160. These protrusions 158, 160 respectively expand the width of the bottom portion of the support member.

As shown in FIGS. 2A and 2B, the base portion 108 preferably comprises a front ledge 162 having a front ledge length that spans along longitudinal axis A-A. A front ledge width 164 fluidly extends from a support member front sidewall 166 to a front base portion sidewall 168. In a preferred embodiment, a chamfered surface 170 may form a transition surface between the front ledge surface 162 and the front base portion sidewall 168. In a preferred embodiment, the chamfer surface 170 has a chamfer angle 172 that ranges from about 30° to about 50°, more preferably the chamfer angle is about 45°.

The rear protrusion 160 extends from the bottom of the base portion 108 of the support bracket 100 as shown in FIGS. 2A, 2S and 4. In a preferred embodiment, the rear protrusion 160 comprises a rear ledge 174, having a rear ledge length 176 that preferably spans the length of the support bracket 100. A rear ledge width 178 extends from a rear support member sidewall 180 to a rear base portion sidewall surface 182. The rear base portion sidewall 182 and the rear ledge 174 meet at about a perpendicular angle thereof.

In a preferred embodiment as shown in FIGS. 2, and 5 to 11 a passageway 184 resides at the bottom of the base portion 108. The passageway 184 forms an opening through which the distal end of the bracket insert 114 is positioned. In a preferred embodiment, the passageway 184 is dimensioned to allow the distal end of the bracket insert 114 to extend therethrough. The passageway 184 preferably extends through a width 186 of the base portion 108. The passageway 184 is further positioned about perpendicular to longitudinal axis A-A. In addition, the passageway 184 is positioned such that it extends at least partially through the bottom surface 110 of the base portion 108. Furthermore, at least one passageway 184 is preferably positioned between two legs 112. In a preferred embodiment, the width of the bottom surface 110 of the base portion 108 approximates the length of the landing surface 142 of the bracket insert 114 (FIG. 4).

As shown in FIGS. 2, 2A, 2B, 4, and 5 to 11, the leg or legs 112 of the anchor mechanism fluidly extends from the bottom surface 110 of the base portion 108. Each leg 112 comprises a leg transition portion 188 spaced from a foot portion 190. As shown, the transition portion 188 extends from the bottom portion of the support member 106 which transitions into the foot portion 190 of the leg 112. In a preferred embodiment, the transition portion 188 is curved such that the support member 106 and the foot portion 190 of the leg 112 are about perpendicular to each other. Although it is preferred that the support member 106 and the foot portion 190 of the leg 112 are oriented about perpendicular to each other, it is contemplated that the foot 190 and support member 106 may be oriented such that they form an acute angle therebetween. In a further preferred embodiment, two legs 112 extend from the bottom portion of the support member 106 with a space 192 residing therebetween. As shown in FIG. 2, each foot portion 190 preferably resides about parallel with imaginary horizontal axis B-B.

In an embodiment, each foot portion 190 comprises a foot length 194, a foot width 196 and a foot height 198. In a preferred embodiment, the foot length 194 ranges from about 0.1 cm to about 5 cm. The foot width 196 may range from about 0.1 cm to about 1 cm and the foot height 198 may range from about 0.1 cm to about 1 cm. It is preferred that the foot portion 190 is dimensioned such that it fits through an opening 200 of the case floor 116 (FIG. 12). The case floor opening 200 may be designed with a number of cross-sectional geometries. For example, the floor opening 200 may be designed with a rectangular, a hexagonal, a triangular, or round cross-sectional geometry. Although each of the feet 190 are illustrated with a rectangular cross-section, it is contemplated that the feet 190 may also be designed with a hexagonal, a triangular, or round cross-section that approximates the cross-sectional geometry of the floor opening 200.

As previously mentioned, extending upwardly from the base portion 108 is the support member 106. The support member 106 comprises opposing support member sidewall surfaces. The support member has a support member length 202 that spans longitudinally along axis A-A, a support member width 204 that extends along axis B-B and a support member height 206 that extends vertically along axis C-C. Specifically, the support member 106 comprises the front support member sidewall 166 spaced apart from the rear support member sidewall 180, with a support member thickness 208 therebetween. In a preferred embodiment, the support member length 202 may range from about 2 cm to about 50 cm, the support member height 206 may range from about 1 cm to about 10 cm and the support member width 204 may range from about 0.1 cm to about 1.0 cm.

Once the leg or legs 112 of the support bracket are positioned through the openings 200 of the floor 116 of the case 102, the bracket insert 114 is positioned through the passageway 184 of the base portion 108. In a preferred embodiment, the bracket insert 114 is designed to interface with the front and rear protrusions 158, 160 of the base portion 108. Specifically, the bracket insert 114 is positioned such that a ridge sidewall surface 210 residing along the width of the second bracket ridge 140 interfaces with a portion of the bottom of the rear base portion sidewall surface 182. On the opposite side, the sidewall surface 156 and the inner sidewall surface 154 of the overhang portion 152 of the bracket insert 114 contact the front sidewall surface 166 and the front ledge 162 of the support member 106 respectively.

As illustrated in FIG. 4, the distal end 122 of the bracket insert 114 is slid through the passageway 184 (FIG. 2) of the base portion 108 between a top surface 210 of the case floor 116 and the support member 106. Once positioned through the passageway 184, the insert ridges 128 preferably reside adjacent to the rear protrusion sidewall surface 182. The bracket insert 114 provides a space positioned between the second ridge 140 and insert sidewall 124 within which the base portion 108 resides. In a preferred embodiment, when the bracket insert 114 is properly positioned, the width 186 of the base portion 108 is positioned along the landing surface 142 of the insert 114.

To release the support bracket 100 from its position within the tray 102, a force is applied to the front sidewall 166 of the support member 106. In a preferred embodiment, the force is applied to the front sidewall 166 of the support member 106 such that the support member 106 is no longer perpendicular to axis B-B. When such a force is applied, the support member assumes a cocked position such that the top portion of the support member 106 is angled towards the distal end of the bracket insert 114. This cocked position angles the support member 106 such that the overhang portion 152 of the bracket insert 114 disengages from the front ledge surface 162 of the base portion 108. In addition, when tilted, the bottom portion of rear sidewall protrusion surface 182 (FIGS. 2A and 2B) no longer contacts the sidewall ridge surface 210. Furthermore, the overhang portion 152 of the insert 114 comes into contact with the chamfered surface 170 of the base portion 108. It is at this point that the bracket insert 114 may be removed from the passageway 184 of the base portion 108. Once the bracket insert 114 is removed, the support bracket 100 may be removed from its current position within the tray 102 and, therefore, may be repositioned to a different location therewithin.

FIGS. 2 and 5 to 11, illustrate various non-limiting forms and geometries with which the support member 106 may embody. As illustrated, the examples shown are generally of a "U", "L", "V" or rectangular shape. The various embodiments of the support member 106 are intended to provide a means to hold, secure, or partition a multitude of different orthopedic tools and devices within the case 102. Since these tools are typically unique, it is contemplated that other forms and geometries of the support member 106 may be used. For example, the support member 106 may be designed with a central opening with a cross-section, that is curved, round, rectangular, triangular, hexagonal, or the like. Furthermore, the support member 106 may be designed with a shape that is generally curved, round, triangular, hexagonal, or the like.

Figure 5:
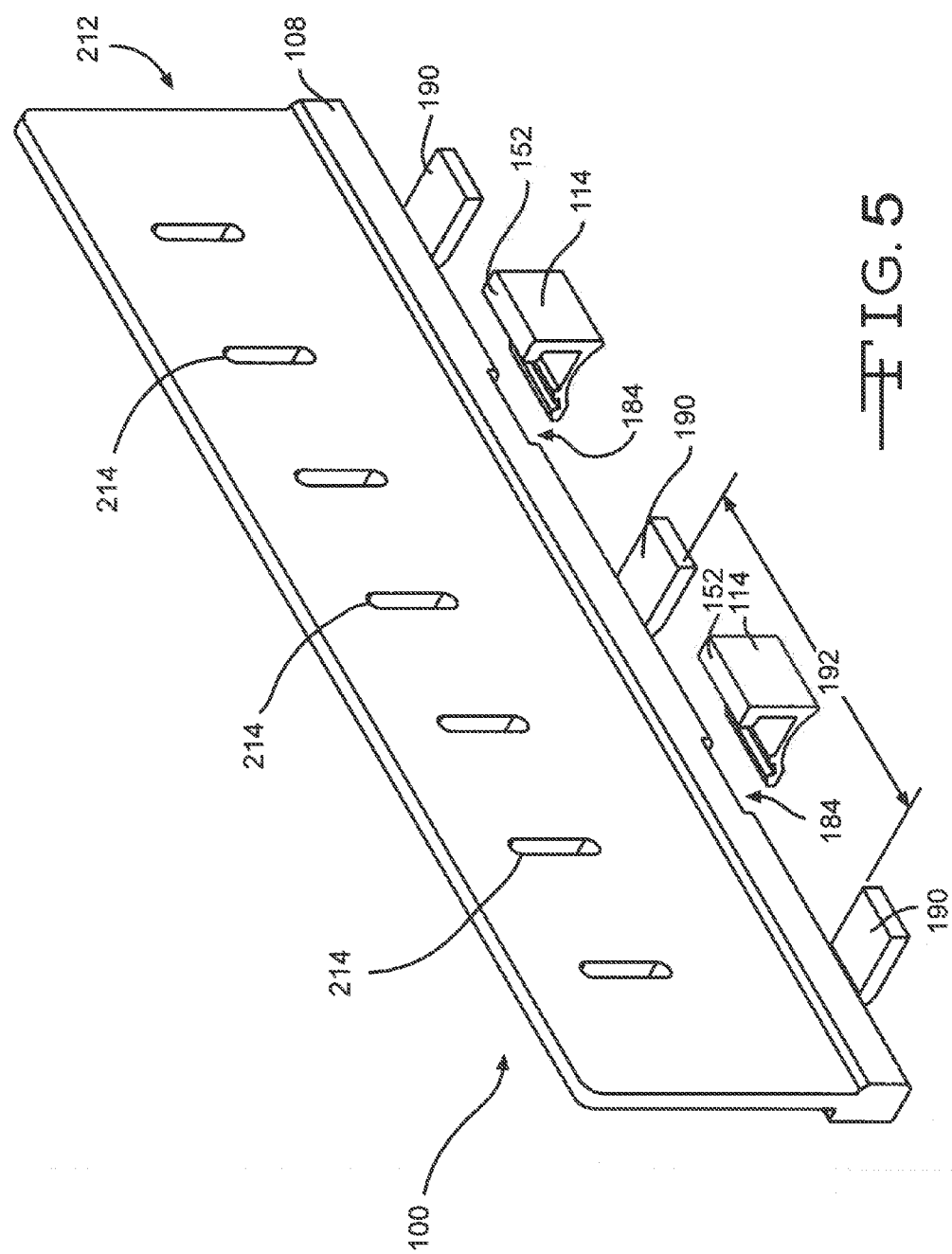
FIGS. 5 to 11 illustrate various perspective views of non-limiting embodiments of the support member portion comprising the support bracket of the present invention.

FIG. 5 illustrates an example of a support bracket 100 with an elongated support member 212. As shown, the support bracket 100 is of a generally rectangular form having a support member 212 that extends along longitudinal axis A-A. In a preferred embodiment, the support member 212 has a series of support member openings 214 positioned periodically along its length, extending through the support member thickness. As shown, these openings 214 are generally of an oval cross-section. Although these openings 214 are illustrated with a generally oval cross-section, the openings 214 may be designed with alternate cross-sectional geometries such as those previously mentioned.

In addition, the exemplar support bracket 212 shown in FIG. 5 utilizes two bracket inserts 114. Furthermore, the support bracket 100 is illustrated with its feet 190 positioned at a greater separation distance as compared to the support bracket illustrated in the previous FIG. 2. The spacing of the feet 190 and the number of bracket inserts 114 contribute to the mechanical and structural stability of the support bracket 100 within the tray or case 102. In general, the longer the length of the support bracket 100, the wider the feet 190 must be spaced apart from each other and/or a greater number of bracket inserts 114 must be utilized to provide increasing structural integrity to the support bracket 100. It is, therefore, contemplated that the support bracket 100 may be designed with a multitude of two or more bracket inserts 114 and that the spacing of the feet 190 may range from about 2 cm to about 20 cm depending on the specific design and application of the support bracket 100.

Figure 6:
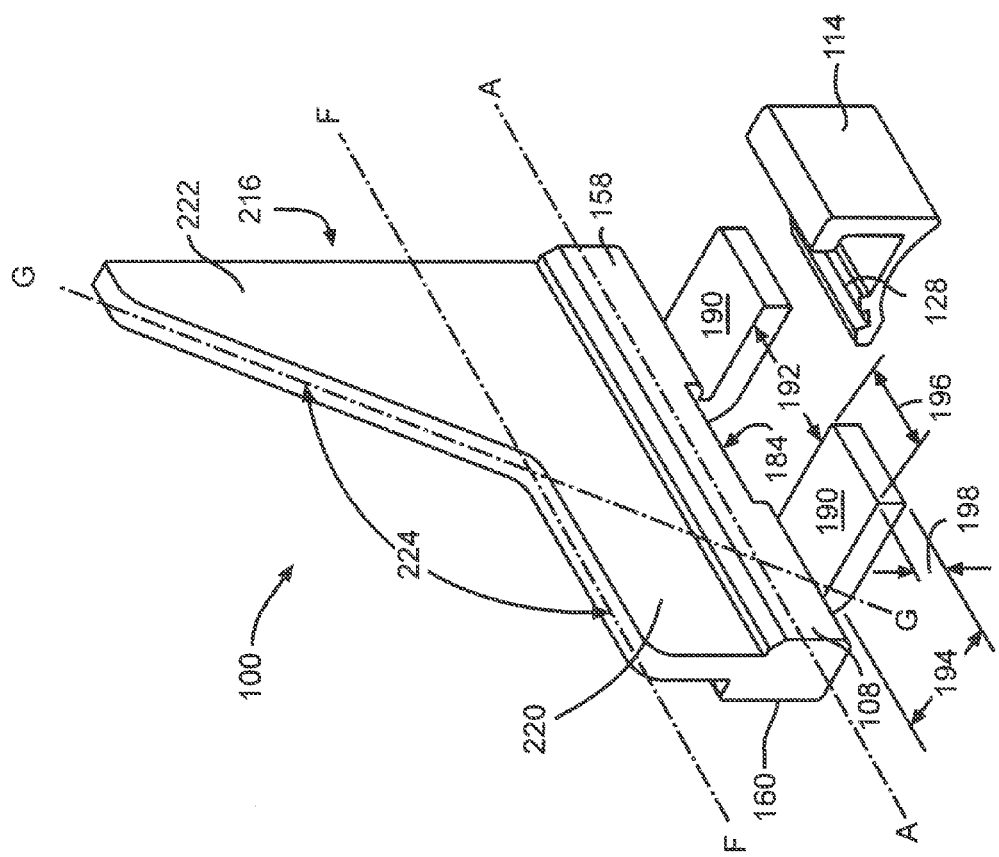
Figure 7:
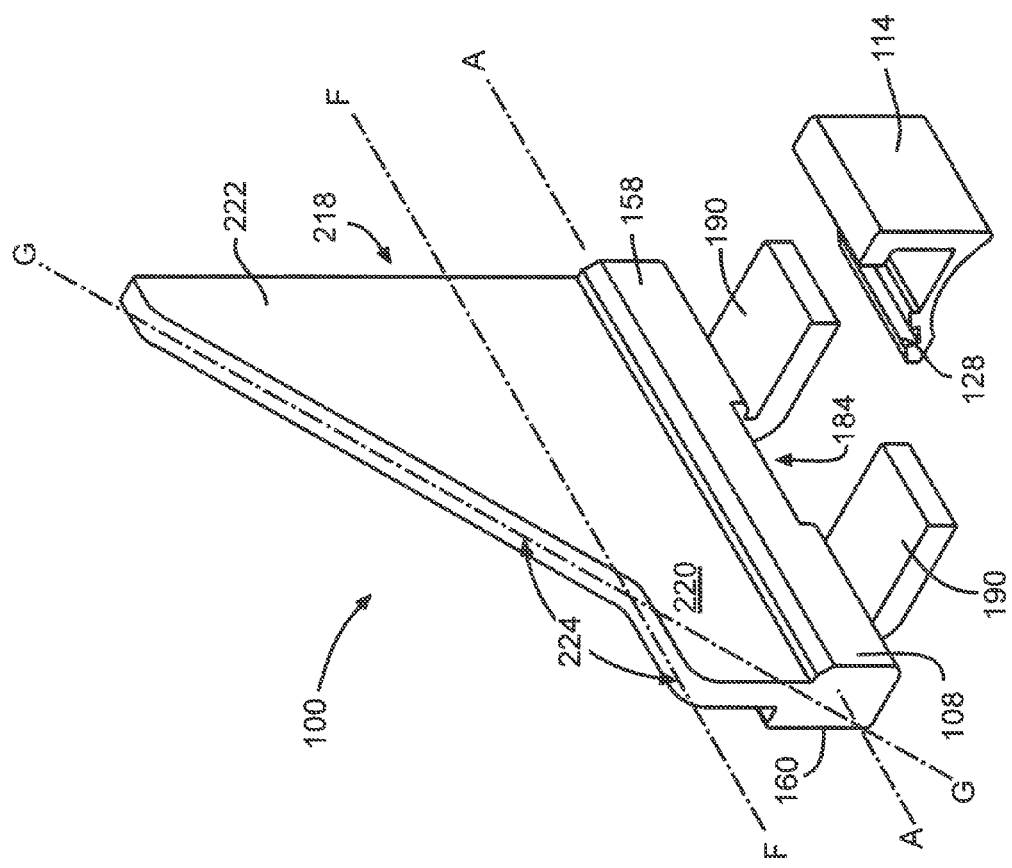

FIGS. 6 and 7 illustrate support brackets 100 of a generally "L" shape geometry. The support members 216, 218 respectively of these brackets 100 have a substantial portion of their sidewalls removed. As shown, a support member "cutout" portion has been removed thereby creating a generally "L" shape support member 216 (FIG. 6), 218 (FIG. 7) comprising respective left and right sidewall portions 220, 222. This "L" shape may be designed with a variety of orientations. As shown, a transition angle 224 exists between the two respective left and right portions 220, 222 that comprise the support member 216, 218. This transition angle 224 largely defines the orientation and appearance of the "L" support member shape. In general, the "L" support member shape may be generally of a right angle or an obtuse angle. Specifically, the transition angle 224 may range from about 90° to about 160°. The transition angle 224 is herein defined as the angle between an imaginary line F-F that extends about parallel to longitudinal axis A-A and an imaginary line G-G that extends tangentially along the opposing surface of the respective opposite side of increasing elevation.

Figure 8:
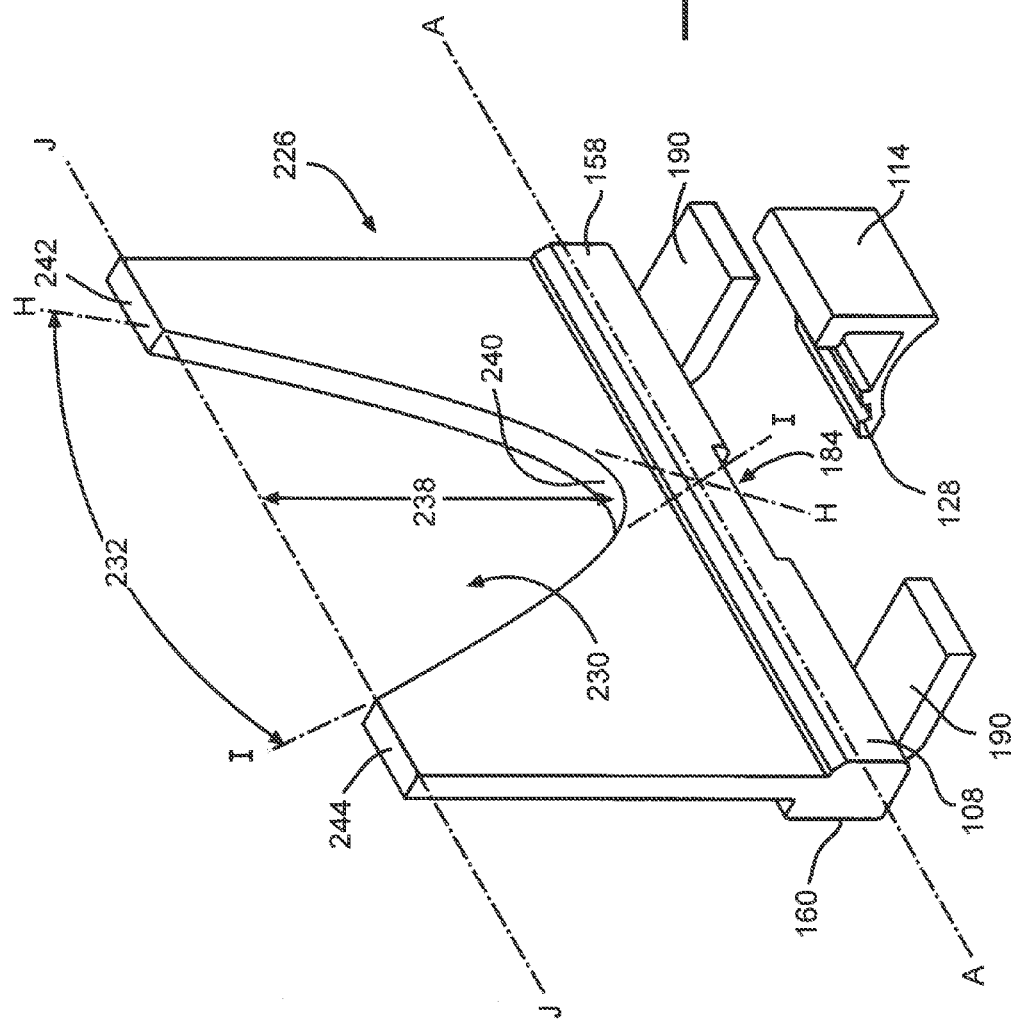
Figure 9:
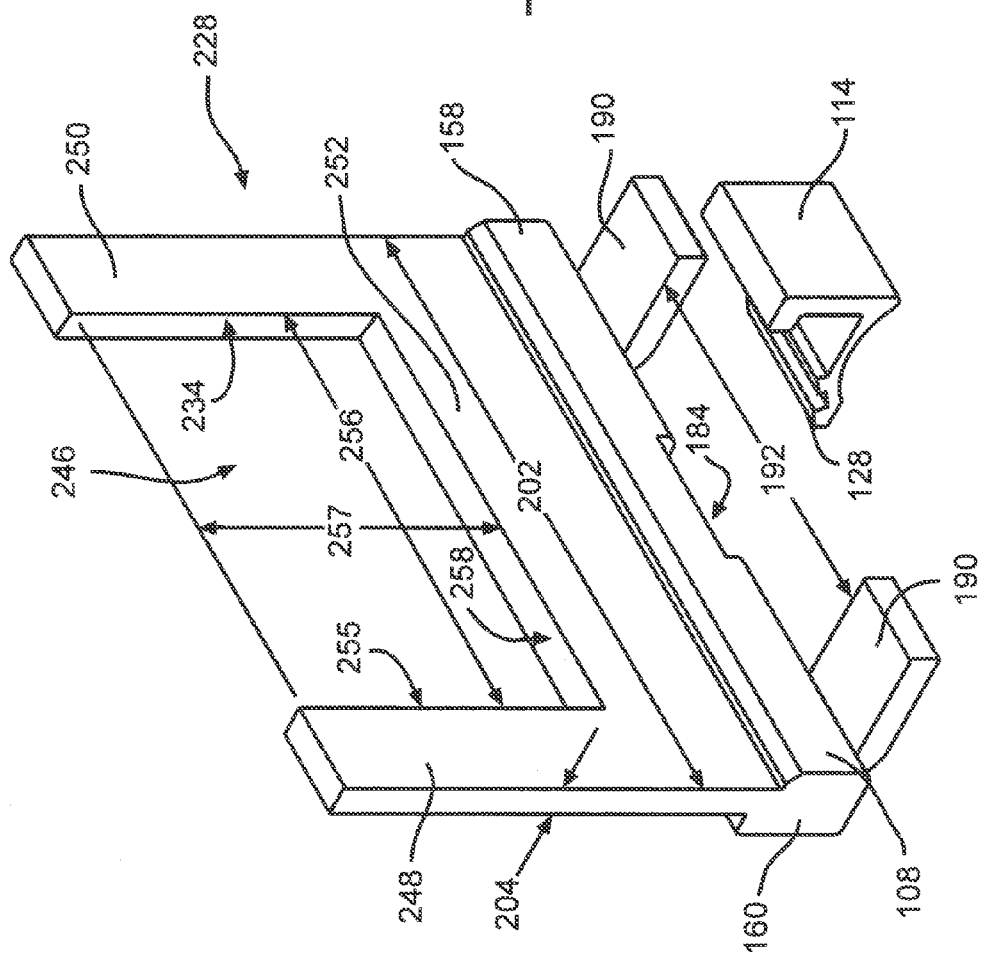

FIGS. 8 and 9 illustrate embodiments of support brackets 100 of a generally "U" shape. As shown the support member 226 of FIG. 8 has a generally curved cutout portion 230 that is centrally positioned within the support member 226. The curved cutout portion 230 may embody a number of any non-limiting forms and geometries. For example, the curved cutout portion 230 shown in FIG. 8 may have an angle of cut that is deeper or shallower than that which is shown. In a preferred embodiment, the curved cutout portion 230 comprises a curved portion having an "angle of cut" 232 ranging from about 20° to about 80°. The "angle of cut" 232 is herein defined as the angle between a first imaginary line H-H that extends tangentially along a left curved surface 234 and a second imaginary line I-I that extends tangentially along a right or opposing curved surface 236. Furthermore, the curved cutout portion 230 comprises a cutout depth 238 extending vertically from a concave point 240 to line J-J that extends parallel to longitudinal axis A-A and tangentially between a right top surface 242 and a left top surface 244 of the support member 226.

FIG. 9 illustrates another embodiment of the support bracket 100 of the present invention. As illustrated, the support bracket 100 comprises a support member 228 having a generally rectangular cutout portion 246 thereby creating two opposing left and right support posts 248, 250, and a bar portion 252 positioned therebetween. It is preferred that an inner right post surface 234 and an inner left post surface 255 respectively form about a perpendicular angle to a top surface 258 of the bar portion 252. In a preferred embodiment, the cutout portion 246 has a cutout portion length 256 that ranges from about 2 cm to about 20 cm and a cutout portion height 257 that ranges from about 1 cm to about 10 cm.

Figure 10:
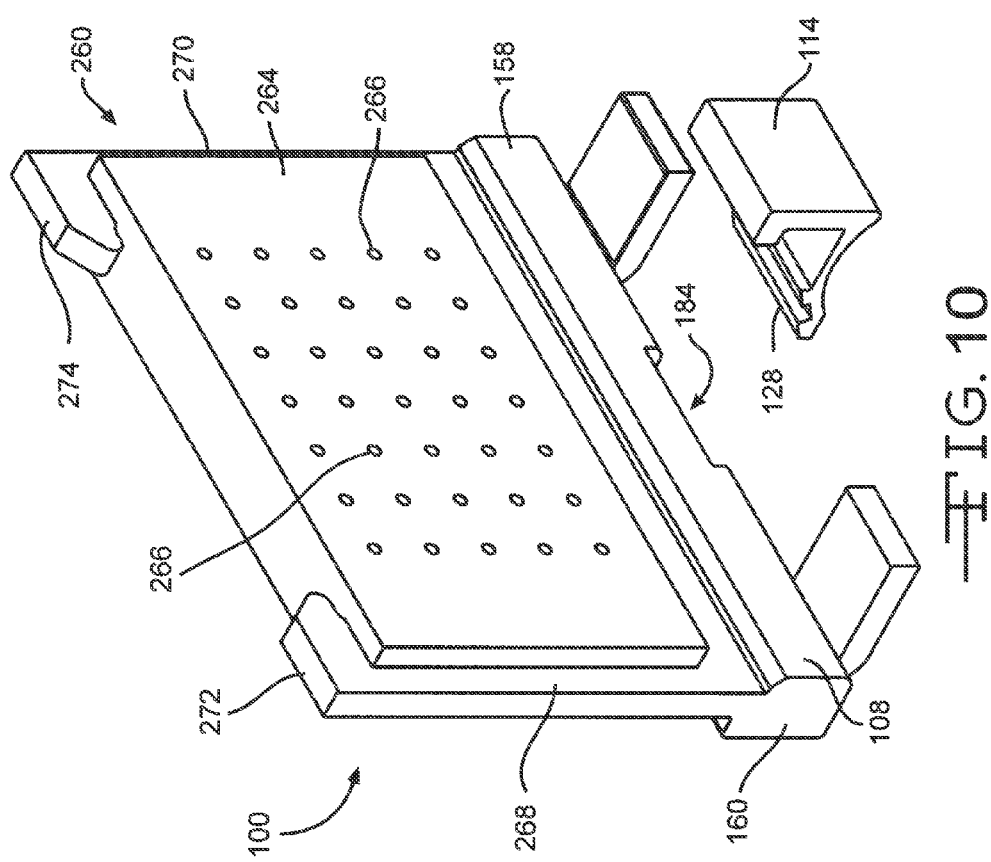
Figure 11:
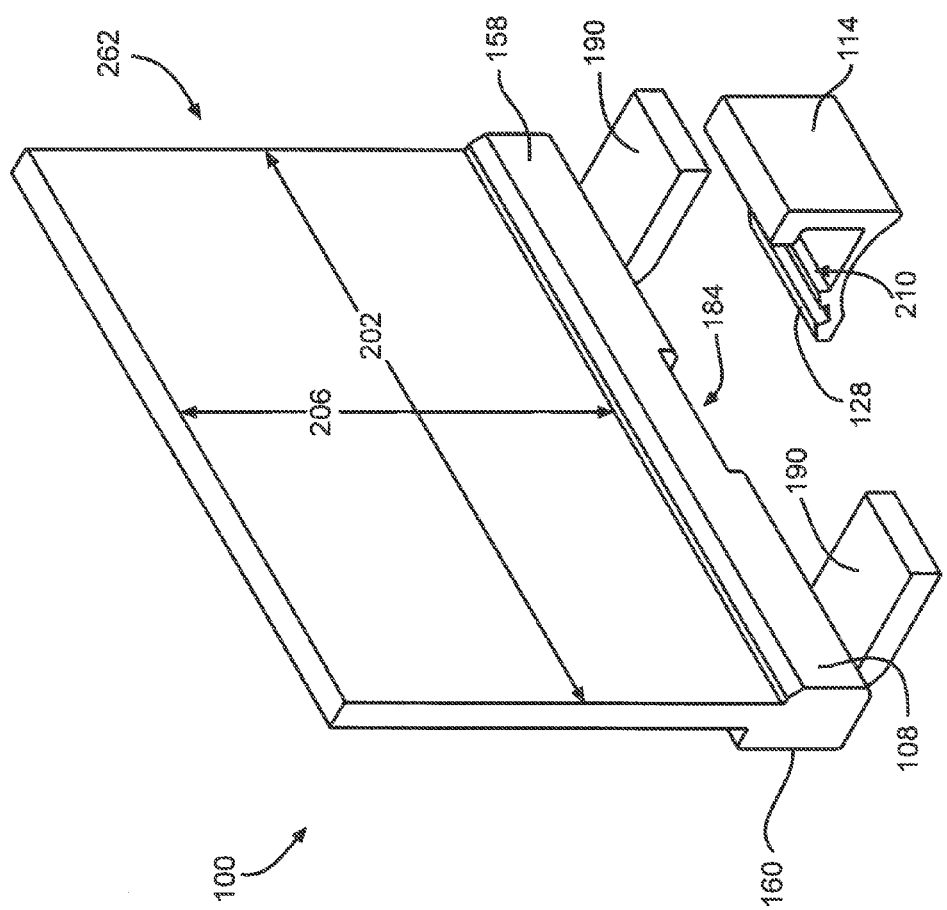
Figure 12:
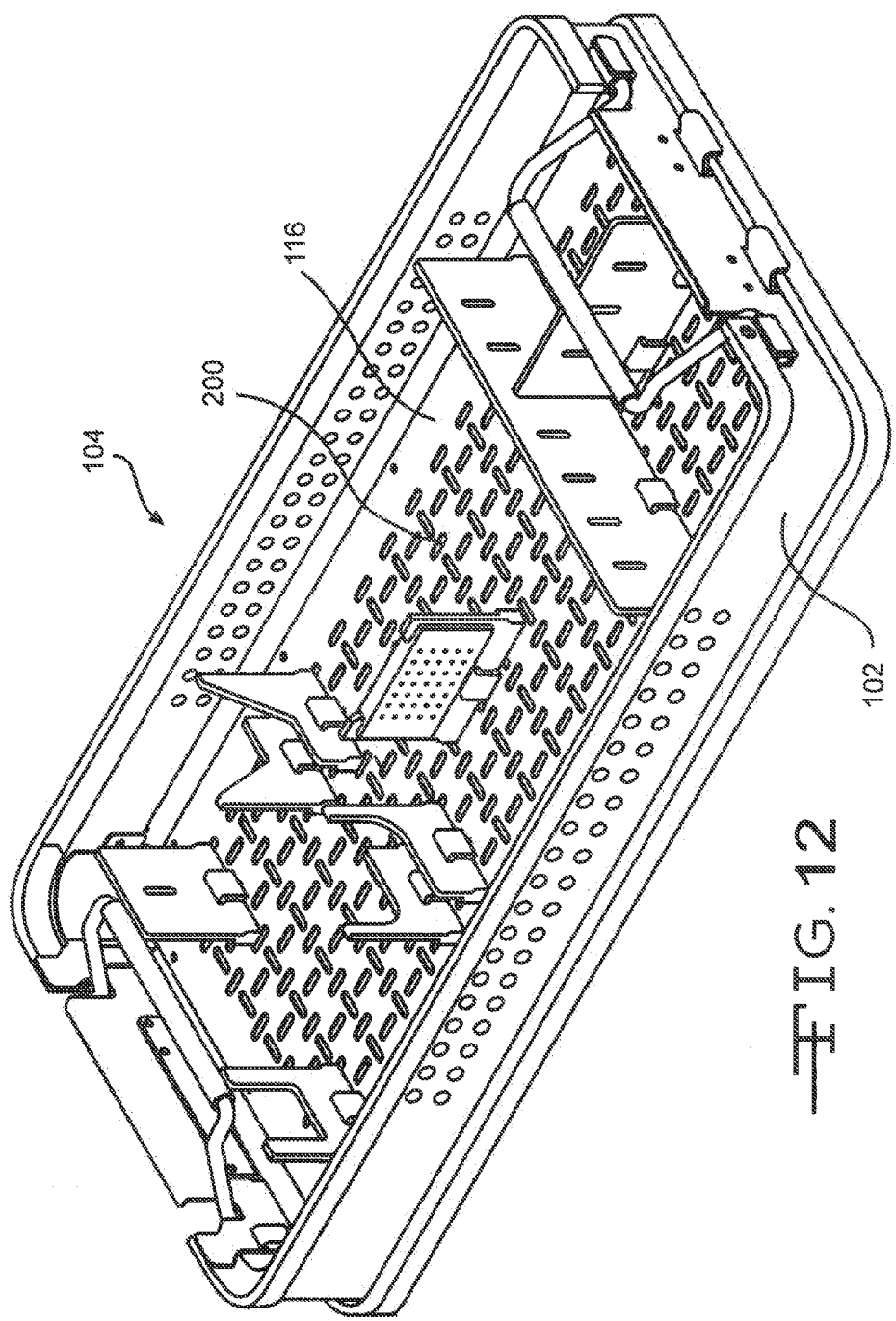
FIG. 12 illustrates a perspective view of a support bracket system comprising a variety of embodiments of the support bracket of the present invention.

FIGS. 10 and 11 illustrate examples of support members 260 and 262 respectively having a generally solid rectangular support member. Specifically, FIG. 10 illustrates an alternate embodiment of support member 260 wherein the support member 260 comprises a removable support insert 264. The support insert 264 having a generally rectangular shape with a series of support insert openings 266 periodically spaced throughout and extending through the thickness of the insert 264. These openings 266 preferably allow for the passage of gases and liquids to pass therethrough, particularly when performing sterilization of the tools (not shown).

In a preferred embodiment, the support insert 264 may be removed from the support bracket 100. As shown, two opposing left and right support posts 268, 270 may be slightly outwardly bent to allow the support insert 264 to be positioned therebetween. Respective left and right clamp portions 272, 274 further hold the support insert therewithin.

FIG. 12 illustrates an embodiment of the modular system of support brackets 104 positioned within the case 102. As illustrated, the various previously described embodiments of support brackets 100 are shown positioned throughout the case 102.

Of course, the forgoing description is that of certain features, aspects and advantages of the present invention, to which various changes and modifications can be made without departing from the spirit and scope of the present invention. Moreover, the support brackets need not feature all of the objects, advantages, features and aspects discussed above. Thus, for example, those of skill in the art will recognize that the invention can be embodied or carried out in a manner that achieves or optimizes one advantage or a group of advantages as taught herein without necessarily achieving other objects or advantages as may be taught or suggested herein. In addition, while a number of variations of the invention have been shown and described in detail, other modifications and methods of use, which are within the scope of this invention, will be readily apparent to those of skill in the art based upon this disclosure. It is contemplated that various combinations or sub-combinations of these specific features and aspects of embodiments may be made and still fall within the scope of the invention. Accordingly, it should be understood that various features and aspects of embodiments may be made and still fall within the scope of the invention. Accordingly, it should be understood that various features and aspects of the disclosed embodiments can be combined with or substituted for one another in order to form varying modes of the discussed modular support bracket system and kit.

What is claimed is:

1. A support bracket system, comprising:
   a) a support member, comprising:
      i) a support sidewall extending upwardly from a support sidewall bottom end to a su port sidewall top end, wherein the support sidewall bottom and top ends extend along a support sidewall width along a longitudinal axis to opposed right and left support sidewall surfaces, and wherein the support sidewall bottom and top ends extend along a support sidewall thickness positioned perpendicular to the longitudinal axis to opposed front and back support sidewall surfaces;
      ii) a base extending upwardly from a base bottom end to a base top end connected to the support sidewall bottom end, wherein the base bottom and top ends extend along a base width along the longitudinal axis to opposed right and left base surfaces and wherein the base bottom and top ends extend along a base thickness positioned perpendicular to the longitudinal axis to opposed front and back base surfaces;
      iii) at least one L-shaped leg comprising a leg transition portion extending downwardly to a foot, wherein the transition portion is connected to the base bottom end with the foot aligned generally perpendicular to the transition portion; and
   b) a bracket an L-shaped insert comprising an insert bottom wall extending from a distal insert end to an intermediate insert portion supporting an upstanding insert sidewall, that extends to a distal insert sidewall end, wherein the insert bottom wall has an arched-shaped bottom surface extending from the distal insert end to the intermediate insert portion, and wherein an upper surface of the insert bottom wall provides a landing surface portion disposed between an upstanding ridge adjacent to the distal insert end and the insert sidewall; and
   c) wherein the foot portion of the leg is positionable through an opening in a support floor with the insert then being positionable between an upper surface of the support floor and the bottom end of the base so that the transition portion of the leg provides that the base of the support member is spaced above the support floor, but with the foot portion of the leg contacting a bottom surface of the support floor opposite the base so that the insert thereby wedges between the support floor and the support member.

2. The support bracket system of claim 1 wherein the support sidewall is generally comprised of a "U" geometry oriented perpendicular to the longitudinal axis.

3. The support bracket system of claim 1 wherein the support sidewall comprises a cutout portion having a cross-section of essentially a "U" geometry oriented perpendicular to the longitudinal axis, the cutout portion extending through the support sidewall thickness and extending from the support sidewall top end to at least partially towards the support sidewall bottom end.

4. The support bracket system of claim 1 wherein the insert distal end is angled in a downward direction with respect to the landing surface portion.

5. The support bracket system of claim 4 wherein the insert distal end is angled at an insert distal end angle, the insert distal end angle measured between the intersection of a first imaginary line that extends along a distal bottom surface of the insert bottom wall distal end to an intermediate bottom surface of the intermediate insert portion and a second imaginary line that extends tangentially along a top surface of the insert distal end.

6. The support bracket system of claim 1 wherein an overhang portion resides at the insert sidewall distal end, the overhang portion extending about perpendicular from the insert sidewall distal end towards the insert distal end, and wherein the overhang portion is contactable to an external surface of the base to thereby provide mechanical stability to the support member.

7. The support bracket system of claim 1 wherein the thickness of the base is greater than the thickness of the support sidewall thereby forming a front base protrusion having a front base protrusion thickness that extends from the support sidewall front surface to the base front surface and forming a rear base protrusion having a rear base protrusion thickness that extends from the support sidewall back surface to the base back surface, wherein at least a portion of the insert is contactable to at least one of the front and rear base protrusions to thereby provide mechanical stability to the support member.

8. The support bracket system of claim 1 wherein the base comprises a front ledge that extends along a top surface of the base top end between the support sidewall front, surface and the base front surface and a rear ledge that extends along the base top surface between the support sidewall back surface and the base back surface, at least a portion of the insert contactable to either the front or rear ledge to thereby provide mechanical stability to the support member.

9. The support bracket system of claim 1 wherein the arched-shaped bottom surface of the insert comprises an archway radius of curvature partially bounded by the insert distal end and the insert intermediate portion, and wherein the archway provides an upward bias force when positioned between the upper support floor surface and the base bottom end to thereby establish a lockable relationship between the support member and the floor surface.

10. The support bracket system of claim 1 wherein at least one of the insert, the support sidewall, the leg, and the base is composed of a polymeric material.

11. The support bracket system of claim 1 wherein a passageway extends upwardly part-way along the base height from the base bottom end toward the base top end and part-way along the base width between the base right and left surfaces, and wherein at least a portion of the L-shaped insert is positionable therewithin to thereby establish a lockable relationship between the support member and the support floor.

12. The support bracket system of claim 1 wherein when the insert is positioned between the base end and the upper support floor surface, the upstanding ridge is positioned adjacent at least one of the front and back base surfaces to thereby provide a lockable relationship between the support member and the support floor.

13. The support bracket system of claim 1 wherein a first thickness between the distal insert end and the intermediate insert portion is greater than a second thickness of the base between the front and back base surfaces to thereby provide mechanical stability to the support member.

14. A support bracket system, comprising:
 a) a support member comprising:
  i) a support member sidewall extending upwardly from a support sidewall bottom end to a support sidewall top end, wherein the support sidewall bottom and top ends extend along a support sidewall width along a longitudinal axis to opposed right and left support sidewall surfaces, and wherein the support sidewall bottom and top ends extend along a support sidewall thickness positioned perpendicular to the longitudinal axis to opposed front and back support sidewall surfaces;
  ii) a base extending upwardly from a base bottom end to a base top end connected to the support sidewall bottom end, wherein the base bottom and top ends extend along a base width along the longitudinal axis to opposed right and left base surfaces and wherein the base bottom and top ends extend along a base thickness positioned perpendicular to the longitudinal axis to opposed front and back base surfaces;
  iii) at least one L-shaped leg comprising a leg transition portion extending downwardly to a foot, wherein the transition portion is connected to the base bottom end with the foot aligned generally perpendicular to the transition portion; and
 b) an L-shaped insert comprising an insert bottom wall extending from a distal insert end to an intermediate insert portion supporting an upstanding insert sidewall that extends to a distal insert sidewall end, wherein the insert bottom wall has an archway having an insert archway radius of curvature partially bounded by the distal insert end and the intermediate insert portion, and wherein an upper surface of the insert bottom wall provides a landing surface portion disposed between the distal insert end and the insert sidewall; and
 c) wherein the foot portion of the leg is positionable through an opening in a support floor with the insert then being positionable between an upper surface of the support floor and the bottom end of the base so that the transition portion of the leg provides that the base of the support member is spaced above the support floor, but with the foot portion of the leg contacting a bottom surface of the support floor opposite the base so that the insert thereby wedges between the support floor and the support member, and wherein the insert archway is positioned between the upper support floor surface and the base bottom end to thus provide an upward bias force against the base to thereby establish a lockable relationship between the support member and the support floor.

15. The support bracket system of claim 14 wherein the support sidewall is generally comprised of a "U" geometry oriented perpendicular to the longitudinal axis.

16. The support bracket system of claim 14 wherein the support sidewall comprises a cutout portion having a cross-section of a "U" geometry oriented perpendicular to the longitudinal axis, the cutout portion extending through the support sidewall thickness and extending at least partially through the support sidewall top end towards the support sidewall bottom end.

17. The support bracket system of claim 14 wherein the bracket insert distal end is angled in a downward direction with respect to the landing surface portion.

18. The support bracket of claim 14 wherein an upstanding ridge positioned adjacent the distal insert end along the upper surface of the insert bottom wall is positionable adjacent either the front or back base surface to thereby establish a lockable relationship between the support member and the support floor.

19. The support bracket of claim 14 wherein the landing surface portion provides a surface on which the base end is positioned to thereby provide mechanical stability to the support member.

20. The support bracket of claim 14 wherein the insert distal end is angled at an insert distal end angle, the insert distal end angle extending between the intersection of a first imaginary line that extends along a bottom surface of the insert, bottom wall distal end and a second imaginary line that extends tangentially along a top surface of the insert distal end, wherein the insert distal end angle ranges from about 20° to about 50°.

21. The support bracket system of claim 14 wherein a passageway extends upwardly part-way along the base height from the base bottom end toward the base top end and part-way along the base width between the base right and left surfaces, and wherein at least a portion of the L-shaped insert is positionable therewithin to thereby establish a lockable relationship between the support member and the support floor.

22. The support bracket system of claim 14 wherein the base comprises a front ledge that extends along a top surface of the base top end between the support sidewall front surface and the base front surface and a rear ledge that extends along the base top surface between the support sidewall back surface and the base back surface, and wherein at least a portion of the insert is contactable to either the front or rear ledge to thereby provide mechanical stability to the support member.

23. The support bracket system of claim 22 wherein an overhang portion resides at the insert sidewall distal end, the overhang portion extending about perpendicular from the insert sidewall distal end towards the insert distal end, and wherein the overhang portion is contactable to at least one of the front and rear ledges to thereby provide mechanical stability to the support member.

24. A support bracket system, comprising:
a) a support member comprising:
i) a support sidewall extending upwardly from a support sidewall bottom end to a support sidewall top end, wherein the support sidewall bottom and top ends extend along a support sidewall width along a longitudinal axis to opposed right and left support sidewall surfaces, and wherein the support sidewall bottom and top ends extend along a support sidewall thickness positioned perpendicular to the longitudinal axis to opposed front and back support sidewall surfaces;
ii) a base extending upwardly from a base bottom end to a base top end connected to the support sidewall bottom end, wherein the base bottom and top ends extend along a base width along the longitudinal axis to opposed right and left base surfaces and wherein the base bottom and top ends extend along a base thickness positioned perpendicular to the longitudinal axis to opposed front and back base surfaces;
iii) at least one L-shaped leg comprising a leg transition portion extending downwardly to a foot, wherein the transition portion is connected to the base bottom end with the foot aligned generally perpendicular to the transition portion; and
b) an L-shaped insert comprising an insert bottom wall extending from a distal insert end to an intermediate insert portion supporting an upstanding insert sidewall extending to a distal sidewall end, wherein the insert bottom wall has an archway having an insert archway radius of curvature partially bounded by the distal insert end and the intermediate insert portion, and wherein an upper surface of the insert bottom wall provides a landing surface portion disposed between an upstanding ridge adjacent to the distal insert end and the insert sidewall; and
c) wherein the foot portion of the leg is positionable through an opening in a support floor with the insert then being positionable between an upper surface of the support floor and the bottom end of the base so that the transition portion of the leg provides that the base of the support member is spaced above the support floor, but with the foot portion of the leg contacting a bottom surface of the support floor opposite the base so that the insert is positioned between the support floor and the support member so that the ridge is positioned adjacent to at least one of the front and back base surfaces, and wherein the archway is positioned beneath the base end to thus provide an upward bias force against the support member base and to thereby establish a lockable relationship between the support member and the support floor.

25. The support bracket system of claim 24 wherein the base portion thickness is greater than the support member thickness thereby forming a front base protrusion having a front base protrusion thickness that extends from the support sidewall front surface to the base front surface and forming a rear base protrusion having a rear base protrusion thickness that extends from the support sidewall back surface to the base back surface, wherein at least a portion of the insert is contactable to at least one of the front and rear base protrusions to thereby provide mechanical stability to the support member.

26. The support bracket system of claim 24 wherein the base comprises a front ledge that extends along a top surface of the base top end between the support sidewall front surface and the base front surface and a rear ledge that extends along the base top surface between the support sidewall back surface and the base back surface, and wherein at least a portion of the insert is contactable to either the front or rear ledge to thereby provide mechanical stability to the support member.

27. The support bracket system of claim 26 wherein an overhang portion resides at the insert sidewall distal end, the overhang portion extending about perpendicular from the insert sidewall distal end towards the insert distal end, and wherein the overhang portion is contactable to at least one of the front and rear ledges to thereby provide mechanical stability to the support member.

28. The support bracket system of claim 24 wherein the first support member portion is generally of a "U" geometry oriented perpendicular to the longitudinal axis.

29. The support bracket system of claim 24 wherein the first support member portion comprises a cutout portion having a cross-section of essentially a "U" geometry oriented perpendicular to the longitudinal axis that extends through the first support member top end and at least partially through the first support member thickness towards the first support member bottom end.

\* \* \* \* \*

UNITED STATES PATENT AND TRADEMARK OFFICE
CERTIFICATE OF CORRECTION

PATENT NO. : 8,827,088 B1  
APPLICATION NO. : 13/300696  
DATED : September 9, 2014  
INVENTOR(S) : John D. Krause and Don E. McGee Page 1 of 1

It is certified that error appears in the above-identified patent and that said Letters Patent is hereby corrected as shown below:

In the Claims

Column 9, line 62 (Claim 1, line 4) delete "su port" and insert --support--

Column 10, line 16 (Claim 1, line 25) after "b)" delete "a bracket"

Column 10, line 18 (Claim 1, line 27) after the word "sidewall" delete the ","

Column 11, line 10 (Claim 8, line 3) after the word "front" delete the ","

Column 12, line 56 (Claim 20, line 5) after the word "insert" delete the ","

Signed and Sealed this  
Nineteenth Day of May, 2015

Michelle K. Lee  
*Director of the United States Patent and Trademark Office*